US00PP36476P2

(12) United States Plant Patent
Nishikawa

(10) Patent No.: US PP36,476 P2
(45) Date of Patent: Feb. 18, 2025

(54) ***DELOSPERMA* PLANT NAMED 'FSDD2117'**

(50) Latin Name: *Delosperma nubigenum*
Varietal Denomination: FSDD2117

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 18/614,655

(22) Filed: Mar. 23, 2024

(30) Foreign Application Priority Data

Jan. 12, 2024 (QZ) ..... PBR 2024/0050

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./422
CPC ... A01H 5/02; A01H 5/12; A01H 5/00; A01H 6/00
See application file for complete search history.

(56) References Cited

PUBLICATIONS

Plantipp *Delosperma* Desert Dancers Purple, retrieved on Jul. 10, 2024 at https://plantipp.eu/uk/varieties/delosperma-desert-dancers-purple-fsdd2117pbr, 3 pp. (Year: 2024).*
Zyromski Unrooted Cuttings 2023-2024, retrieved on Jul. 10, 2024 at https://www.zyromski.com/wp-content/uploads/2023/10/SFZ-BDC-2023-2024-Quality-Cuttings-KD.pdf, 13 pp. (Year: 2024).*

* cited by examiner

*Primary Examiner* — June Hwu
(74) *Attorney, Agent, or Firm* — Penny J. Aguirre

(57) ABSTRACT

A new cultivar of *Delosperma* plant named 'FSDD2117' that is characterized by its purple flowers with red centers, its unique foliage colors; green and pink tones in late winter and early spring, changing to dark green with dark purple in spring and summer, changing to green with red-purple in late summer, its good branching habit, its short stem internodes, its very floriferous and long blooming habit; blooming from early summer into autumn, its ease of growing with no need for vernalization, and its high tolerance to heat, drought, and humidity.

3 Drawing Sheets

Botanical classification: *Delosperma nubigenum.*
Variety denomination: 'FSDD2117'.

BACKGROUND OF THE INVENTION

The present invention relates to a new and distinct cultivar of *Delosperma* plant, botanically known as *Delosperma nubigenum* 'FSDD2117' and will be referred to hereinafter by its cultivar name, 'FSDD2117'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with short stem internodes, good branching, easy rooting, cold hardiness, and unique flower and foliage coloration.

'FSDD2117' was selected in the Inventor's trial garden in 2018 as a single unique plant from amongst the seedlings derived from crosses made in 2016 between unnamed and unpatented plants from the Inventor's breeding program.

Asexual propagation of the new cultivar was first accomplished by stem cuttings in October of 2019 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar.

These attributes in combination distinguish 'FSDD2117' as a unique cultivar of *Delosperma.*

1. 'FSDD2117' exhibits purple flowers with red centers.
2. 'FSDD2117' exhibits unique foliage colors; green and pink tones in late winter and early spring, changing to dark green with dark purple in spring and summer, changing to green with red-purple in late summer.
3. 'FSDD2117' exhibits a good branching habit.
4. 'FSDD2117' exhibits short stem internodes.
5. 'FSDD2117' exhibits a very floriferous and long blooming habit; blooming from early summer into autumn.
6. 'FSDD2117' exhibits ease of growing with no need for vernalization.
7. 'FSDD2117' exhibits a high tolerance to heat, drought, and humidity.

The parent plants of 'FSDD2117' are both similar to 'FSDD2117' in ease of rooting and in plant habit. The parent plants of 'FSDD2117' both differ from 'FSDD2117' in having foliage coloration that is lighter red-purple, longer stems, less cold tolerance, and flowers that are light lavender in color. 'FSDD2117' can be most closely compared to the *Delosperma* cultivars 'DSAB13-1' (U.S. Plant Pat. No. 27,056) and 'T1854' (U.S. Plant Pat. No. 34,730). Both 'DSAB13-1' and 'T1854' are similar to 'FSDD2117' in having floriferous and long blooming habits. 'DSAB13-1' differs from 'FSDD2117' in having smaller leaves and flowers with petals that are bright red-purple in color, white petaloids with light purple tips, and yellow anthers. 'T1854' differs from 'FSDD2117' in having flowers that are larger in size and flowers that are violet-purple in color.

'FSDD2117' can also be compared to the co-pending cultivar of *Delosperma nubigenum* 'FSDD2112'. 'FSDD2112' is similar to 'FSDD2117' in having short internodes, ease of growing with no need for vernalization, a high tolerance to heat, drought, and humidity, a floriferous and long blooming habit, and similar foliage coloration. 'FSDD2112' differs from 'FSDD2117' in having red flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp, Facebook, matteoragni, Promessedefleurs, Myplant & Garden, IPM ESSEN 2024, and Gabot.

BRIEF DESCRIPTION OF THE DRAWINGS

The accompanying color photographs illustrate the overall appearance and distinct characteristics of the new *Delosperma*. The photographs were taken of 3-month-old plants of the new cultivar as grown in a greenhouse in 12-cm pots in Sabaudia, Italy.

The photograph in FIG. 1 provides a top view of 'FSDD2117' in summer.

Figure 1:
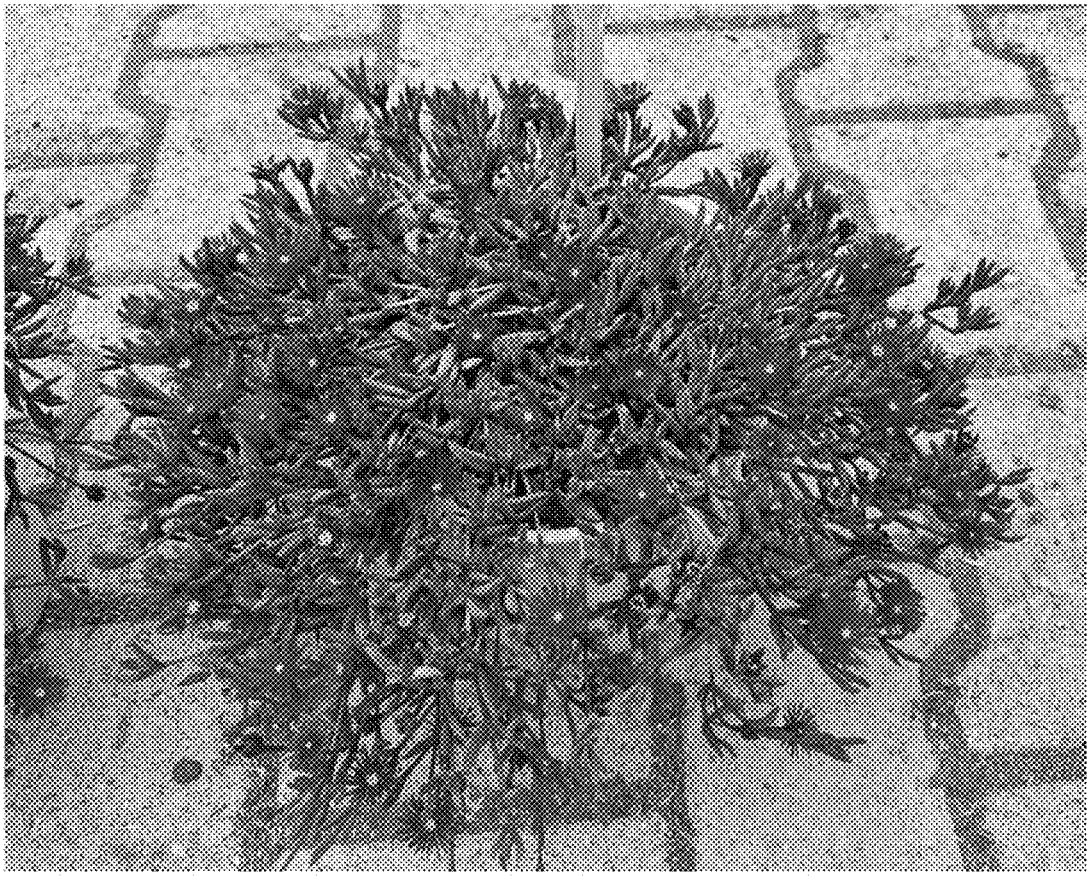
Figure 2:
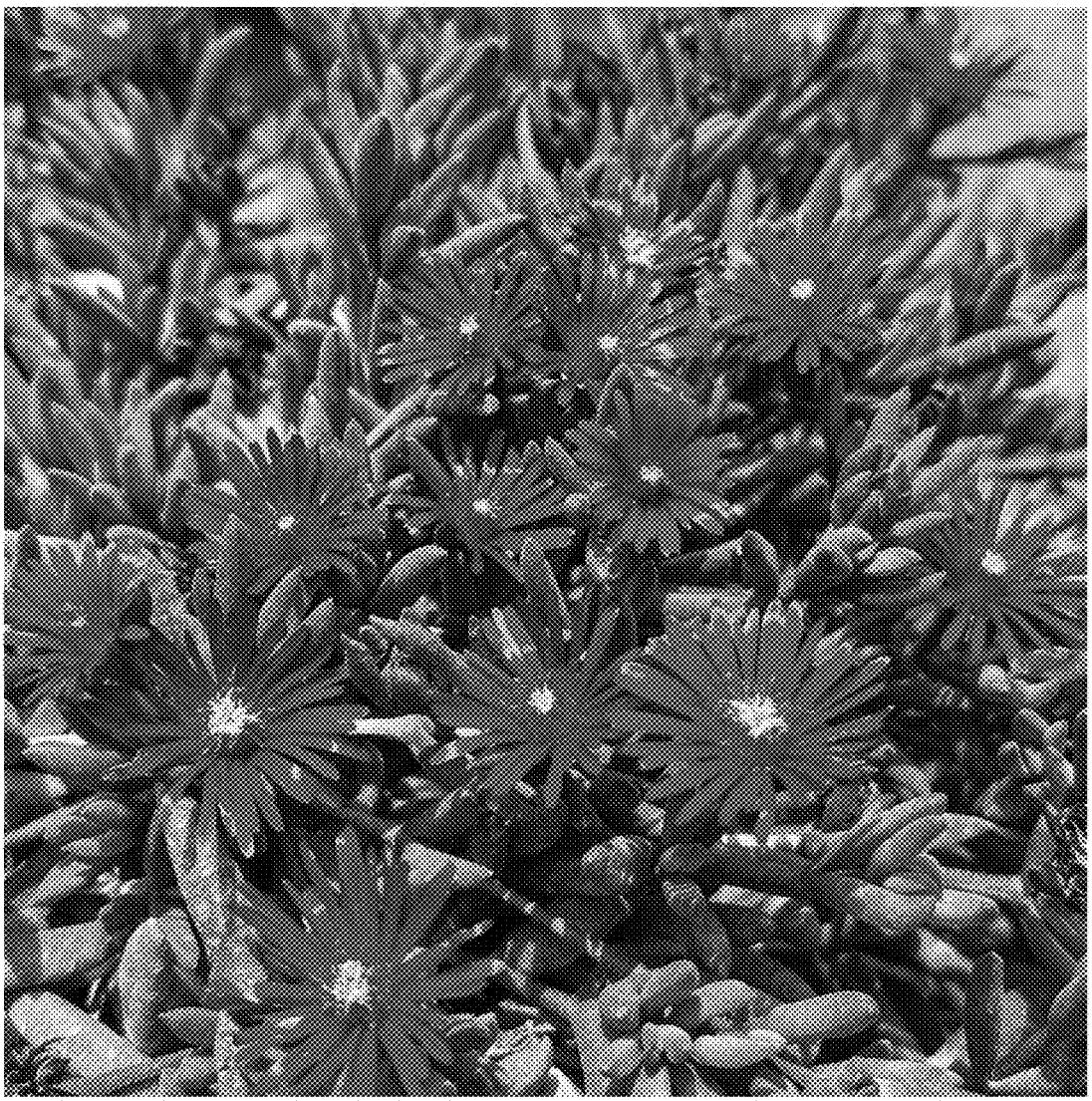

The photograph in FIG. 2 provides a close-up view of the flowers of 'FSDD2117'.

Figure 3:
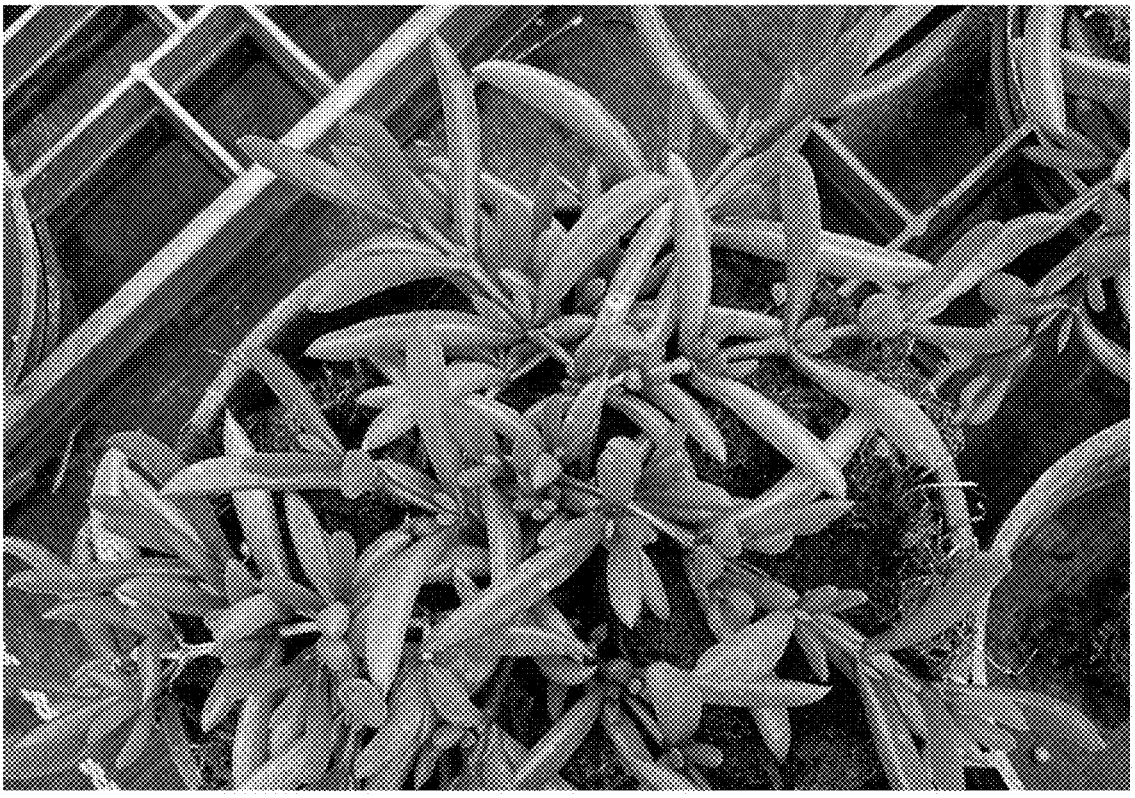

The photograph in FIG. 3 provides a close-up view of the foliage of 'FSDD2117' in late winter and early spring.

The colors in the photographs are as close as possible with the digital photography and printing techniques utilized and the color codes in the detailed botanical description accurately describe the new *Delosperma*.

DETAILED BOTANICAL DESCRIPTION

The following is a detailed description of 4-month-old plants of the new cultivar as grown in a greenhouse in 15-cm pots in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early summer into autumn in The Netherlands.

*Plant type*.—Evergreen perennial.

*Plant habit*.—Flattened, dense, rounded.

*Height and spread*.—Reaches an average of 10 cm in height and 29 cm in width as a 4-month-old plant grown in a container.

*Cold hardiness*.—Observed to be hardy to at least U.S.D.A. Zone b 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a plug to young plant in a P9 container.

*Growth habit*.—Moderate.

Stem description:

*Shape*.—Round.

*Stem color*.—Young; 187C to 187D, young woody stems; 199C, mature and woody stems; 199A and N199A.

*Stem size*.—Lateral branches; an average of 17 cm in length and 3 mm in diameter.

*Internode length*.—An average of 3 cm.

*Stem substance*.—Succulent.

*Stem surface*.—Moderately glossy, moderately pubescent with very short glandular hairs; an average of 0.2 mm in length and closest to 155C in color.

*Branching habit*.—Densely branched, 1 main branch, 4 secondary branches per main branch, 10 tertiary branches per secondary branch.

Foliage description:

*Leaf shape*.—Ligulate.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, slightly pubescent with very short glandular hairs; an average of 0.2 mm in length, matches surface color.

*Leaf color*.—Late winter/early spring; NN74A becoming 145A to 145B with hints of faded NN74A to NN74B, late spring/summer; 137C, base 187C, maturing to 189A, occasionally flushed with 187B and N187B, base 187B, the mature foliage color is retained in fall and winter.

*Leaf size*.—Up to 3.2 cm in length and 8 mm in width.

*Leaf quantity*.—10 per lateral branch.

*Leaf attachment*.—Sessile.

Inflorescence description:

*Inflorescence type*.—Flowers solitary, terminal.

*Flower number*.—An average of 1 per lateral stem.

*Flower fragrance*.—None.

*Flower aspect*.—Slightly outward to upright.

*Flower longevity*.—A few days, self-cleaning.

*Flower type*.—Single.

*Flower size*.—Average of 2.3 cm in diameter and 1.2 cm in depth.

*Flower buds*.—Broadly ovate to oblong in shape, an average of 8 mm in length, 6 mm in diameter, color; N78A, surface is smooth.

*Calyx*.—Rotate in shape, average of 6 mm in depth and 1.4 cm in diameter.

*Sepals*.—5, rotate, ovate in shape, margin entire, an average of 6 mm in length and 2mm in width, broadly acute apex, broadly cuneate base, surface is smooth and dull, color; young upper and lower surface 137D, flushed with N187A and N187B, mature upper surface 137C and N187A to N187B, mature lower NN137A, flushed with 187A and 187B.

*Petals*.—An average of 46 per flower, rotate and slightly curved downward, oblanceolate in shape, surface is moderately glossy on both surfaces, margin entire, apex obtuse, base cuneate, an average of 1.3 cm in length and 1.5 mm in width, color; opening and fully open upper and lower surface N78A and N57A near base.

*Petaloids*.—An average of 20 to 26 per flower, rotate and near vertical surrounding stamens, lanceolate in shape, moderately to highly glossy on both surfaces, margin entire, apex obtuse, base truncate, an average of 5 mm in length and 1 mm in width, color; N78A and N57A near base.

*Peduncle*.—Average of 3.2 cm in length and 2 mm in diameter, straight on top of lateral branch at 0°, 187C to 187D in color, surface moderately glossy, sparsely to moderately pubescent with very short glandular hairs.

*Pedicel*.—None.

Reproductive organs:

*Pistils*.—5, an average of 2 mm in length, stigma; triangular shaped, style and stigma; (not distinguishable) combined an average of 3 mm in length, N144A to N144B in color, ovary; 4 mm in length and width, 143B in color.

*Stamens*.—Average of 60, anthers; dorsifixed and narrowly oblong in shape, an average of 0.5 mm in diameter, 6A in color, filaments; 3 mm in length, N78B in color, pollen; moderate to high in quantity and 6A in color.

*Fruit*.—Fruit and seed production has not observed under the conditions tested.

It is claimed:

1. A new and distinct variety of *Delosperma* plant named 'FSDD2117' as described and illustrated herein.

* * * * *